(12) United States Patent
Stevens (10) Patent No.: US 9,782,291 B2
(45) Date of Patent: Oct. 10, 2017

(54) INTRAOCULAR IMPLANT AND METHOD FOR FIXING SAME INTO AN EYE

(76) Inventor: Julian Douglas Stevens, London (GB)

(*) Notice: Subject to any disclaimer, the term of this patent is extended or adjusted under 35 U.S.C. 154(b) by 0 days.

(21) Appl. No.: 13/492,662

(22) Filed: Jun. 8, 2012

(65) Prior Publication Data

US 2013/0331939 A1    Dec. 12, 2013

(51) Int. Cl.
*A61F 9/00* (2006.01)
*A61F 2/16* (2006.01)
*A61F 2/14* (2006.01)
*A61F 9/007* (2006.01)

(52) U.S. Cl.
CPC ............ *A61F 9/0017* (2013.01); *A61F 2/14* (2013.01); *A61F 2/16* (2013.01); *A61F 2/15* (2015.04); *A61F 9/007* (2013.01); *A61F 2002/169* (2015.04)

(58) Field of Classification Search
CPC .............. A61F 2/1453; A61F 2002/169; A61F 2002/1689; A61F 2/16015; A61F 2/1605; G02C 7/048
USPC .................................................. 623/5.15, 6.4
See application file for complete search history.

(56) References Cited

U.S. PATENT DOCUMENTS

| | | | |
|---|---|---|---|
| 4,206,518 A | 6/1980 | Jardon | |
| 4,262,370 A | 4/1981 | Harstein | |
| 4,485,498 A | 12/1984 | Gimbel | |
| 4,642,114 A * | 2/1987 | Rosa | 623/6.15 |
| 5,697,973 A | 12/1997 | Peyman | |
| 6,051,024 A | 4/2000 | Cumming | |
| 6,537,316 B1 * | 3/2003 | Chambers | 623/6.17 |
| 2005/0256570 A1 | 11/2005 | Azar | |
| 2005/0288697 A1 * | 12/2005 | Tei et al. | 606/166 |
| 2006/0058812 A1 | 3/2006 | Terwee | |
| 2006/0142856 A1 * | 6/2006 | Willis et al. | 623/6.36 |
| 2007/0088433 A1 | 4/2007 | Esch | |
| 2008/0269883 A1 * | 10/2008 | Das et al. | 623/6.17 |
| 2010/0036488 A1 * | 2/2010 | de Juan, Jr. | A61F 2/14 623/5.16 |
| 2010/0152847 A1 | 6/2010 | Padrick et al. | |
| 2012/0078363 A1 * | 3/2012 | Lu | 623/6.37 |

OTHER PUBLICATIONS

European Application No. 10251497.3-2320, European Search Report dated Feb. 2, 2011, 8 pages.

* cited by examiner

*Primary Examiner* — Leslie Lopez
(74) *Attorney, Agent, or Firm* — Patterson Thuente Pederson, P.A.

(57) ABSTRACT

An intraocular implant for use in a surgical procedure such as a cataract operation, or in a refractive-lens exchange surgery procedure, has a main portion and a peripheral portion peripheral to the main portion. The main portion is plate-like in shape and may be a lens or a plug for closing an aperture in the capsule of the eye. The implant has two or more lugs extending from the peripheral portion in a direction substantially perpendicular to a plane of the main portion. The lugs extend either from haptics, which protrude from the main portion, or from a short extension of the edge of the main portion. A method for fixing the implant into the eye involves making two or more voids in the capsule wall, offering up the implant to the capsule, so that the lugs lie adjacent to the voids, and inserting the lugs into the voids.

8 Claims, 9 Drawing Sheets

PRIOR ART

Fig. 1

PRIOR ART

PRIOR ART

PRIOR ART

Fig. 4

PRIOR ART

Fig. 5

PRIOR ART

INTRAOCULAR IMPLANT AND METHOD FOR FIXING SAME INTO AN EYE

FIELD OF THE INVENTION

The invention relates to an intraocular implant, and in particular to an intraocular implant for use in cataract operations or refractive crystalline lens extraction operations. The invention also relates to a method for fixing such an intraocular implant into an eye.

BACKGROUND OF THE INVENTION

Figure 1:
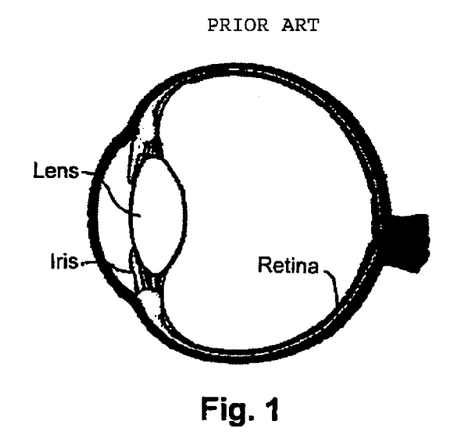
FIG. 1 is a sectional view of the human eye.

The cataract condition is a well known eye ailment, which these days is easily treatable through surgery. The condition involves an opacification, yellowing or clouding of the natural crystalline lens (see FIG. 1), which is situated just behind the iris and serves to focus the incoming image onto the retina at the back of the eye.

The surgical procedure involves the removal of the opaque lens and its substitution by an artificial lens having the required focusing effect.

Figure 2:
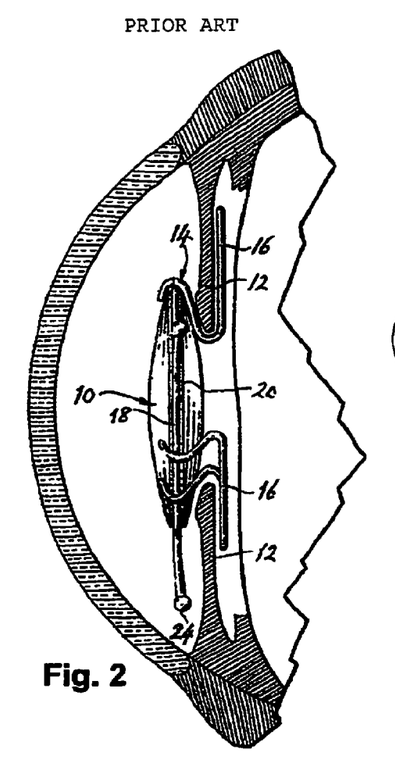
FIG. 2 is a part-side and part-sectional view of a human eye with an artificial lens substituted for the original lens in accordance with a known method.
Figure 3:
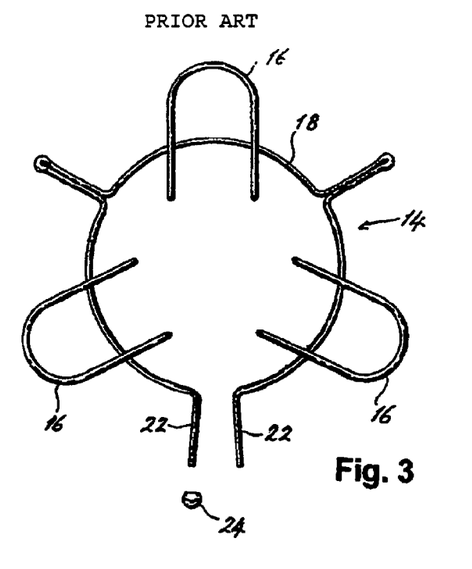
FIG. 3 shows a haptic arrangement used in the known method of FIG. 2.

One way of achieving this is described in U.S. Pat. No. 3,925,825. FIGS. 2 and 3 correspond to FIGS. 1 and 2 of this patent, and show the placing of a lens 10 anterior to the iris 12. The lens is held in place against the iris by a haptic section 14. The haptic section 14 consists of a series of bent wire loops 16, which are attached to a circular wire frame 18. The lens 10 has a flat circumferential face 20 and the lens is held within the frame 18 by inserting the lens inside the frame 18 and closing the legs 22 of the frame so that the frame 18 closes tightly against the lens face 20. Once the legs 22 have been brought together, their ends are kept together via a terminal part 24.

Figure 4:
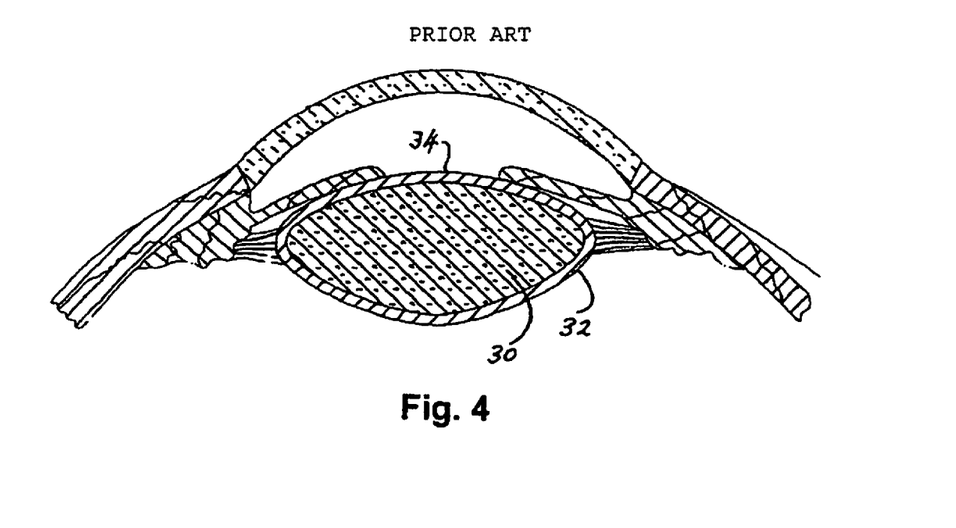
FIG. 4 is a sectional view of a human eye showing the natural lens in its capsule.

One way of extracting the opaque natural lens—a process known as extra-capsular extraction—will now be described. Reference is first made to US 2003/0130732, FIG. 1 of which corresponds to FIG. 4 of the present application. The lens 30 is accommodated within a so-called capsule (also sometimes referred to as a "capsular bag", or simply "bag"), which is shown as item 32 in FIG. 4. To remove the opaque lens, an opening (a so-called "capsulotomy") is made in the anterior part 34 of the capsule 32 manually by a surgeon or by a pulsed laser and the lens 30 is removed through the opening.

To facilitate the removal of the opaque or cloudy lens, the lens is first emulsified by the phacoemulsification method or by a pulsed laser. Phacoemsulification involves making a small incision in the cornea and introducing a very thin needle through the incision, which is then brought into contact with the lens through the capsulotomy. The needle is caused to vibrate at an ultrasonic frequency by the use of a magnetostrictive driver. The ultrasonic vibrations of the needle soften the lens and emulsify it. The emulsified parts can then be aspirated out of the capsule through the incision. Finally, the incision is widened sufficiently to introduce the substitute artificial lens into the capsule. A pulsed laser can be used to create an opening in the capsule, by photoablating capsular tissue along a predetermined boundary, which can be circular or elliptical if desired.

Figure 5:
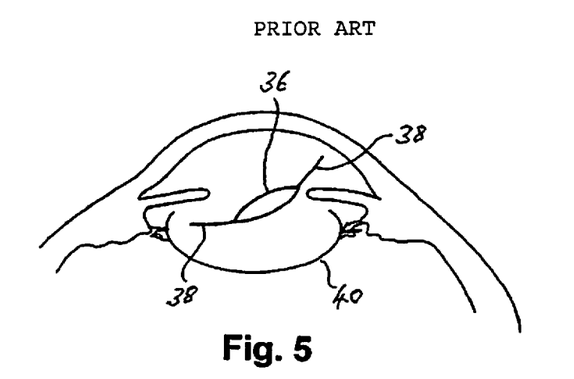
FIGS. 5 and 6 are sectional views showing two stages in a known lens replacement method employing extra-capsular extraction.
Figure 6:
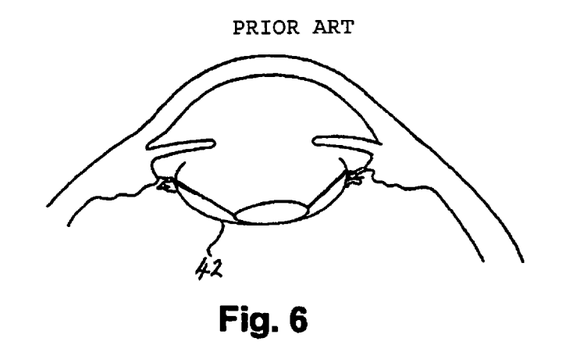

Like the lens of FIG. 2, the lens in the extra-capsular method is conventionally held within the capsule by the use of haptics. One example of this is shown in U.S. Pat. No. 5,376,115. FIGS. 5 and 6 are an extract from this patent, in which the artificial lens 36 with its haptics 38 is introduced through the iris and into the capsule 40 via the capsulotomy (FIG. 5) and finally brought to bear against the inside posterior surface of the capsule (FIG. 6). The haptics 38 are used to center the lens and secure it in place inside the capsule.

SUMMARY OF THE INVENTION

Figure 7:
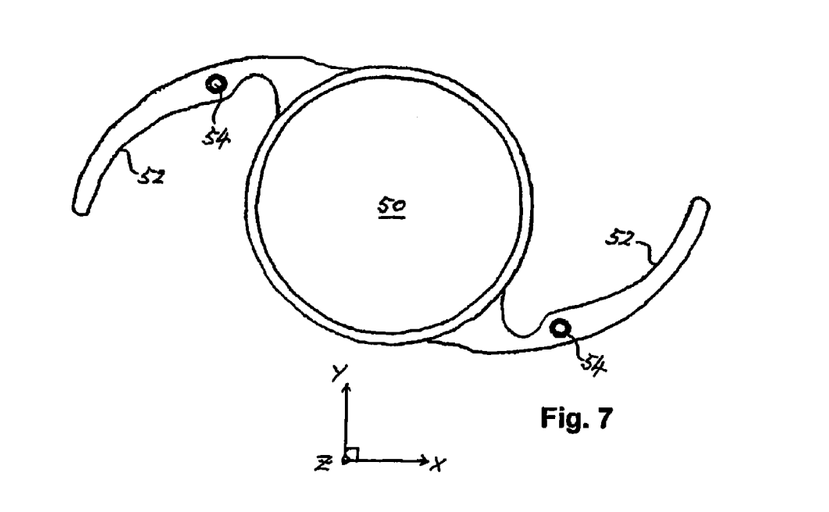
FIGS. 7 and 8 are front and top views, respectively, of an intraocular implant in accordance with an example embodiment of the invention.
Figure 8:
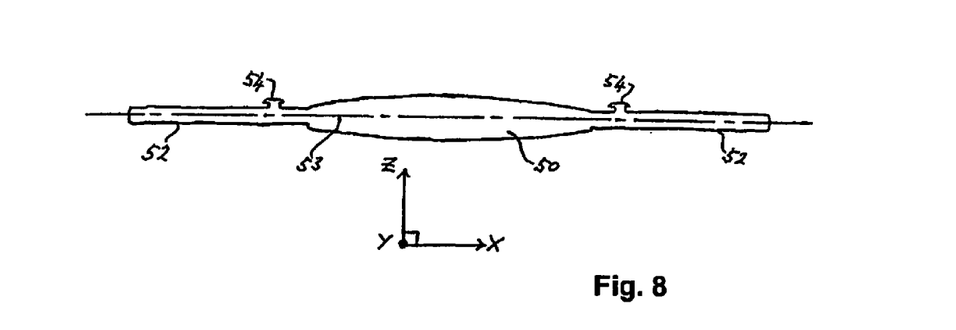

One problem associated with the known capsular insert technique is that it is difficult to centre the lens accurately in the X-Y plane of the eye. (The X-Y-Z co-ordinates are shown in FIGS. 7 and 8.) This is the case, even though the haptics are supposed to centre the lens as close to the optical axis of the eye as possible. The reason for this is that the pupil of the eye, which is the opening of the iris, is not necessarily centered with respect to the capsule. Hence the lens can be centered with respect to the capsule, but not with respect to the pupil.

It is also difficult to ensure that the lens has the desired placement in the rotational direction in the X-Y plane. A third problem is that, due to the presence of the haptics, the known technique requires a fairly large incision in the eye in order to be able to introduce the implant into the eye, whereas it is always desirable to be able to minimize the degree of intervention, including the size of the incision.

A further drawback is the difficulty of accurately defining the location of the lens in the Z-direction. This can lead to difficulties in defining the required optical power of the lens.

It is an aim of the intraocular implant according to the present invention to mitigate drawbacks associated with the known implant techniques.

The present invention provides an intraocular implant for placement in the eye, the implant comprising a main portion, which is a lamina, and a peripheral portion peripheral to the main portion, the implant having at least two lugs extending from the peripheral portion in a direction substantially perpendicular to a plane of the lamina, the lugs being for engagement with corresponding voids provided in a capsule of the eye.

The peripheral portion may comprise at least two haptics extending from the main portion, the haptics comprising respective lugs extending from the haptics in said direction substantially perpendicular to the plane of the lamina.

The peripheral portion may comprise a short extension of the main portion over the entire periphery of the main portion, the extension of the main portion comprising the at least two lugs. This configuration is potentially more compact than the haptic-based configuration. According to one example embodiment, the lugs are substantially equidistantly spaced around the peripheral portion. This allows for greater stability of attachment of the implant to the capsule.

The at least two lugs may each comprise a neck portion, which extends from the peripheral portion in the direction substantially perpendicular to the plane of the lamina, and a head portion extending from the neck portion. The head portion may be mushroom-shaped or otherwise larger than the neck portion, which allows for easier and more secure attachment of the implant to the capsule.

The neck portion may have a length, in the direction substantially perpendicular to the plane of the lamina, approximately equal to the thickness of a wall of the capsule. This length may be in a range 30 to 50 micrometers for example. In addition, the neck portion may have a diameter in a range 100 to 500 micrometers for example.

The implant may take the form of a lens, in which case the main portion of the implant will comprise the optic of the lens. Alternatively, the implant may be a plug for occluding an opening in the capsule of the eye. The plug may have no optical power and may or may not be opaque.

The present invention also provides a method for fixing the intraocular implant into an eye, the method comprising: forming voids within the capsule of the eye, the number of voids corresponding to the number of lugs of the implant; orienting the implant proximate to the capsule, so that the lugs face toward respective voids, and inserting the lugs into the voids, thereby securing the implant to the capsule.

In this method, the at least two lugs may each comprise a neck portion, which extends from the peripheral portion in the direction substantially perpendicular to the plane of the lamina, and a head portion extending from the neck portion, and wherein the lugs are inserted, head portion first, into the voids, the head portion being such as to discourage the implant from coming away from the capsule.

Before the orienting step, there may be the step of surgically removing the natural crystalline lens material of the eye, and, when the capsule is evacuated of the natural crystalline lens material, fixing the implant onto the capsule from either inside or outside the capsule.

BRIEF DESCRIPTION OF THE DRAWINGS

Embodiments of the present invention will now be described, by way of example only, with reference to the drawings, in which:

FIGS. 9(a)-9(e) are enlarged views of different versions of the lug shown in FIGS. 7 and 8;

DETAILED DESCRIPTION

FIGS. 7 and 8 show an intraocular lens comprising the lens proper (the "optic") 50 and a pair of haptics 52. The optic is a lamina, i.e. roughly plate-shaped, so that its diameter (assuming a circular profile) is much greater than its thickness, especially at the edges. Extending from each haptic at a point part-way along its length is a lug 54. The lugs are configured in this example as shown in, e.g., FIG. 9(a) and have a neck 56 and a head 58 and are of one piece with the respective haptics. The lugs extend in a direction substantially perpendicular to the plane 53 of the lamina. In one example of its use, the lens is inserted into the capsule of the eye through a capsulotomy previous made in the eye and is secured to the capsule by inserting each lug through a void made in the capsule by suitable means. In this respect convenient use can be made of the modern femtosecond pulsed laser technique, which enables voids of very accurate size and location to be made in the capsule by laser-pulse photoablation along a predetermined boundary. This means that the lens can be produced as a standard item with the lugs 54 disposed at a standard distance apart from each other and from the optical centre of the optic, leaving it up to the surgeon to form voids of the correct location and size in the capsule to suit this standard distance.

Figures 9A, 9E:
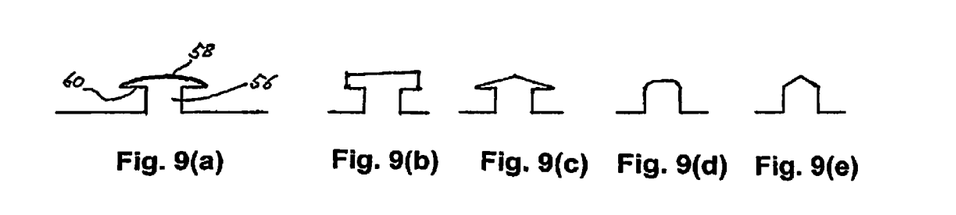

The head 58 of the lugs is preferably, but not necessarily, mushroom-shaped (see FIG. 9(a)), which facilitates the insertion of the lug into the void made in the capsule. By contrast the surface 60 of the head behind the mushroom surface is desirably linear, to discourage the lug from coming out of the void of its own accord. Thus, the void will normally be a through-hole of a diameter approximately equal to that of the neck of the lug. In addition, the neck of the lug will normally be of a length approximately the same as, but preferably somewhat greater than the anticipated thickness of the capsule wall (which is approximately 20 micrometers). A typical range of values for the length of the neck is 30 to 50 micrometers and for the diameter of the neck is 100 to 500 micrometers.

The profile of the lugs may be other than mushroom-shaped, provided it allows relatively easy insertion of the lugs into the voids in the capsule wall. Thus, the lug may have a "T"-shaped cross-section, as shown in FIG. 9(b). A preferred variant of this "T" profile is FIG. 9(c), in which the outer edge is chamfered, making it easier to insert. Also, while the inclusion of a head is to be preferred, for the reason given in the preceding paragraph, it is not absolutely essential. Thus, the invention also envisages the use of a lug as shown in FIG. 9(d) or FIG. 9(e). In FIG. 9(d) the lug consists of just the neck, which has a square top. A variant of this, similar to that shown in FIG. 9(c), is a rounded-top version illustrated in FIG. 9(e). Where the lug is headless, it may be expedient to ensure a fairly tight fit between the lug and the capsule void, in order to discourage migration of the implant away from the capsule.

As regards the profile of the lugs in plan view (view orthogonal to the sectional view of FIG. 9), this is preferably circular, though other profiles may also be suitable.

Figure 10:
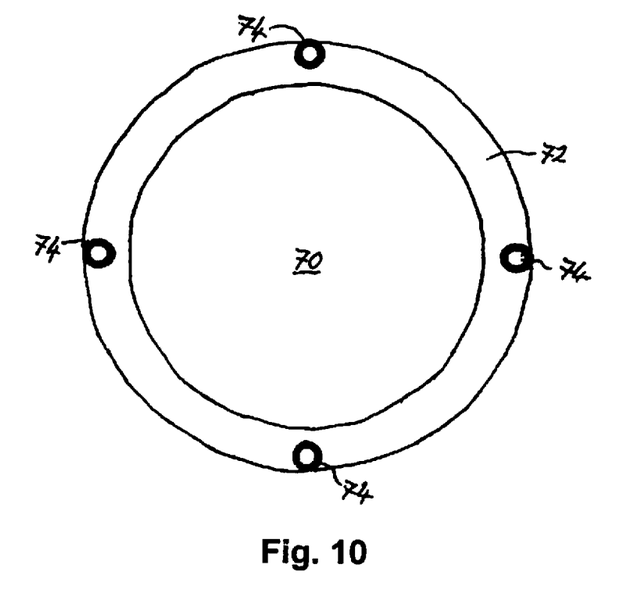
FIGS. 10 and 11 are front and top views, respectively, of an intraocular implant in accordance with another example embodiment of the invention.
Figure 11:
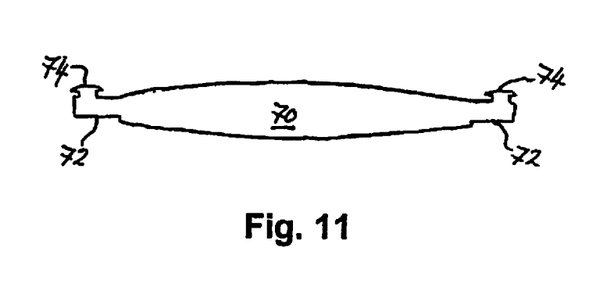

A second embodiment of the implant in accordance with the invention is illustrated in FIGS. 10 and 11.

Here the implant has no haptics, but consists of the optic 70 plus a peripheral section 72, which is a simple extension of the edge of the optic 70. The radial width of the extension will be at least sufficient to accommodate the lugs and to ensure that the voids made in the capsule are reasonably remote from the lip of the capsulotomy. Four lugs 74 protrude from, and are of one piece with, the peripheral section, being substantially equidistantly spaced around the peripheral section. The lugs 74 are configured as in the first embodiment (see FIG. 9).

This implant is smaller than that of the first embodiment, since no haptics are present. This means that the incision to be made in the eye, in order to introduce the implant into the eye, can be made smaller, with a smaller wound and leading to a faster recovery of the patient and less induced astigmatism.

When the implant is located adjacent to the inside of a capsulotomy made in the anterior part of the capsule (an "anterior capsulotomy")—this location is called the "bag fixated" location—the lugs will face toward the front of the eye. This situation applies to the first embodiment, since it assumes the use of haptics, and also to the second embodiment. In addition the lugs can be placed on the posterior side of the device and be fixated in the bag using posterior facing lugs and voids in the posterior capsule. There may or may not be a posterior capsulotomy separate from the voids to receive the lugs. In addition, where the implant of the second embodiment is located adjacent to the outside of the anterior capsulotomy (the "sulcus fixated" location), the lugs will be facing toward the back of the eye. The reverse will apply where the implant is located adjacent the inside or outside of a posterior capsulotomy.

Examples of the above-described first and second embodiments are shown in FIGS. 12-19.

Figure 12:
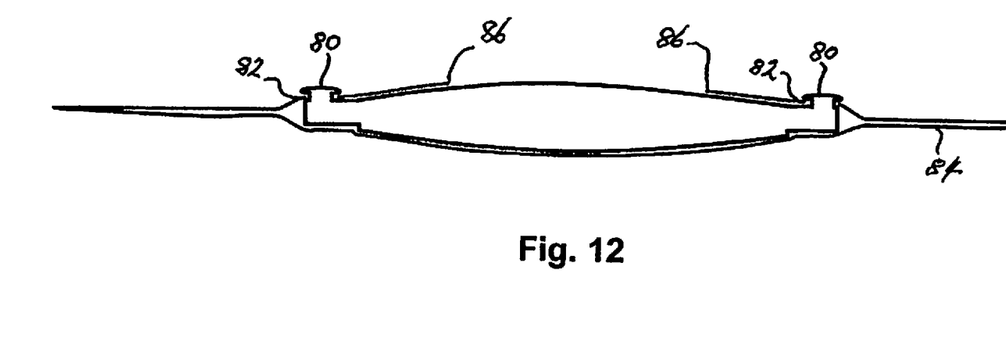
FIGS. 12-19 are various examples of lenses in place in a lens capsule.
Figure 13:
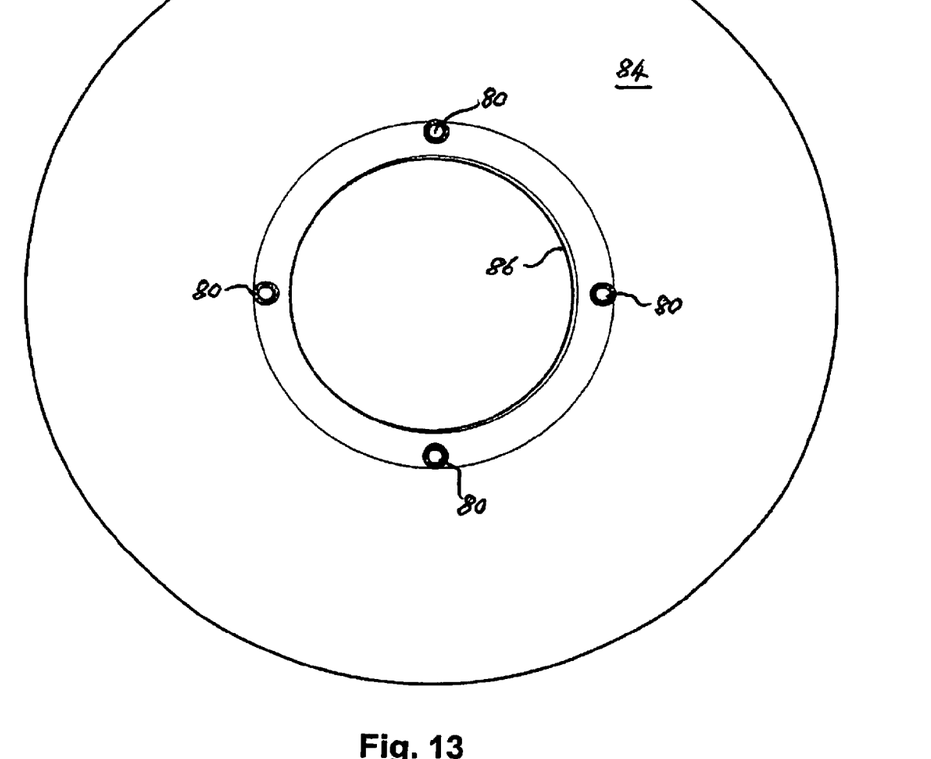

FIG. 12 shows a side view of a lens without haptics located within a capsular bag. The lugs 80 are anterior-facing, i.e. facing toward the front of the eye, and are engaged with holes 82 created in the anterior wall of the bag 84. An anterior capsulotomy 86 can also be seen. FIG. 13 shows a front view of this arrangement, though with a somewhat wider capsulotomy 86 than that shown in FIG. 12.

Figure 14:
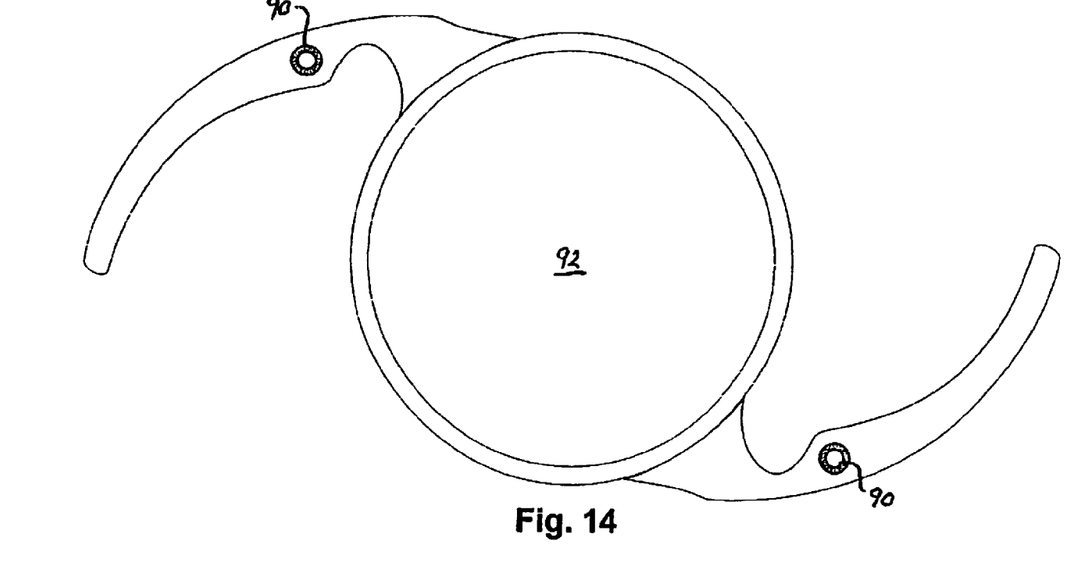
Figure 15:
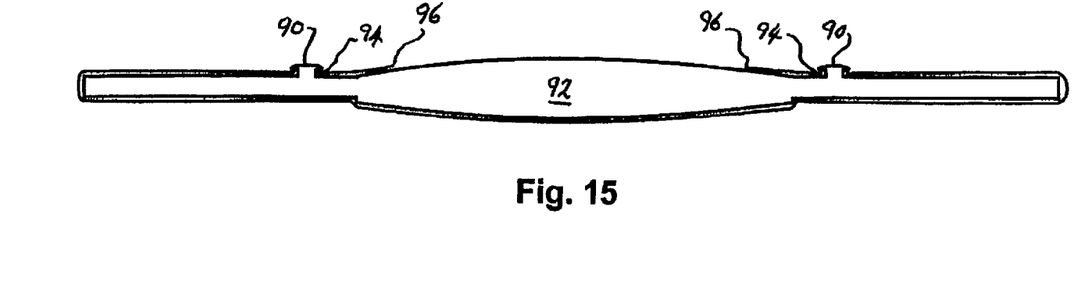

A similar configuration, but involving a lens with haptics, is shown in FIGS. 14 and 15. The lens itself is shown in FIG. 14, while the lens in the bag is shown in FIG. 15. This time the lugs 90 are situated further away from the centre of the lens 92 and therefore engage with holes 94 located further away from the anterior capsulotomy 96.

Figure 16:
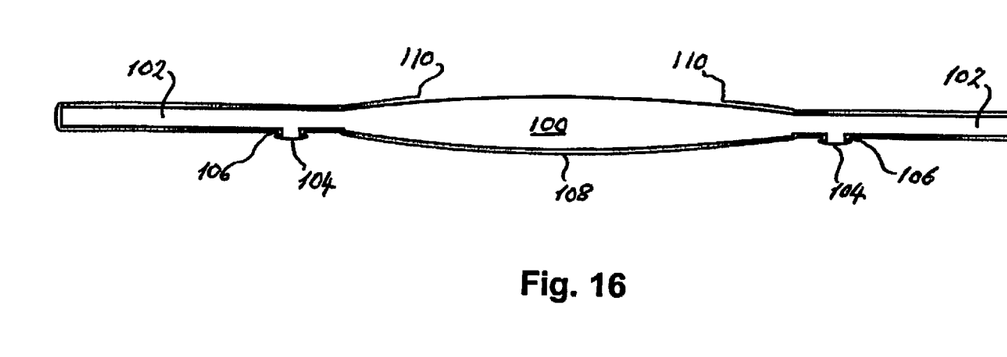

FIG. 16 depicts a side view of a lens 100 with haptics 102 and posterior-facing lugs 104, which engage with holes 106 made in the posterior wall 108 of the bag. Also shown is an anterior capsulotomy 110.

Figure 17:
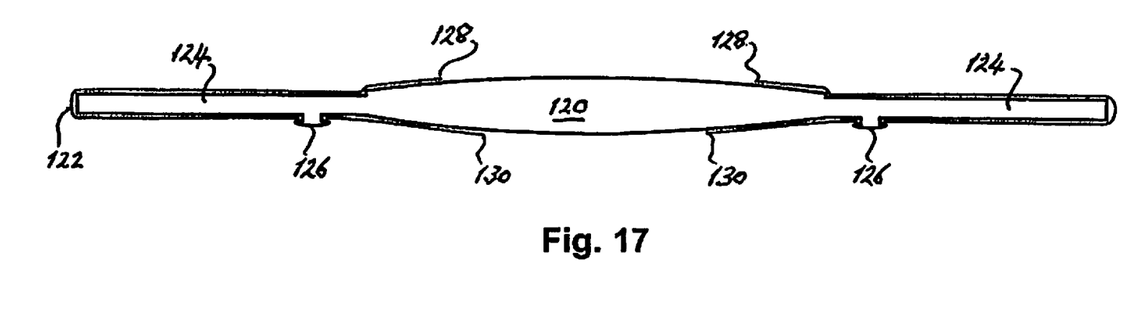
Figure 18:
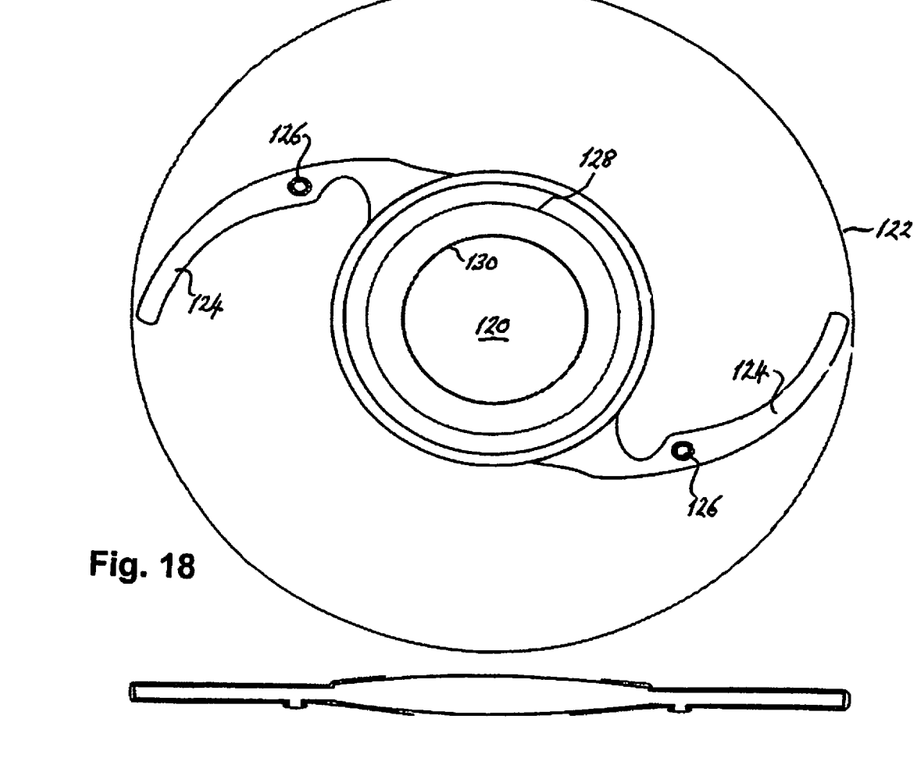

FIGS. 17 and 18 are top and front views, respectively, of a lens 120 located in the capsular bag 122, in which the lens has haptics 124 and posterior-facing lugs 126 inserted into posterior capsular voids. This time a capsulotomy 128, 130 has been made in both the anterior and posterior walls of the capsule. Incidentally, FIG. 18 shows, for clarity, a copy of FIG. 17, but with reduced dimensions to align with the diameter of the capsular bag shown in FIG. 18.

Figure 19:
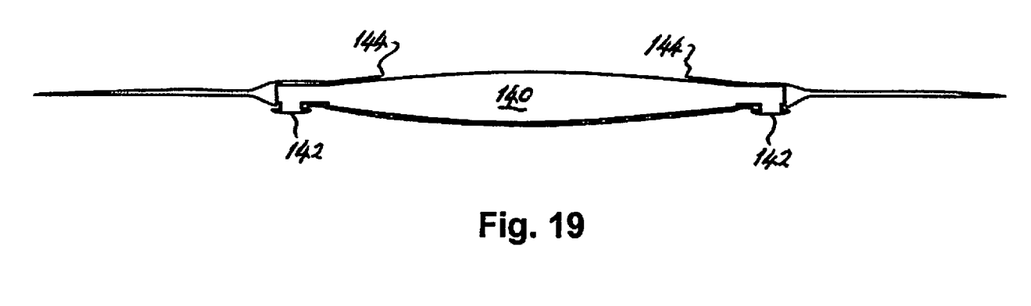

Finally, an example of a hapticless lens 140 having posterior-facing lugs 142 engaging posterior voids is shown in FIG. 19. The capsular bag has an anterior capsulotomy 144.

The use of the lugs in these two embodiments has the following advantages:
  the implant can be reliably and repeatedly placed at a desired position in the X-Y plane vis-à-vis the capsule;
  the implant can be very securely attached to the capsule;
  the implant can be fixed at a desired rotational orientation, which is required where the lens has an asymmetrical optic (e.g. where there is variable optical power in the lens or where there is a toric optic);
  since the implant can be held firmly against the capsule by the lugs (via the mushroom head), the implant can be made to have a well defined placement in the Z-direction (see FIG. 8), which enables a reliable definition of the optical power of the implant to be obtained.

Instead of using only one lens as an implant, it may be necessary to employ a multi-lens design. Examples of such a design are illustrated and discussed in US 2003/0130732 mentioned earlier, the contents of which are incorporated by reference. The multiple lens form a unit and are secured to the capsule via either anterior-facing or posterior-facing lugs. Alternatively, both anterior and posterior facing lugs may be provided on respective front and back lenses, these lugs engaging with voids made in the anterior and posterior walls of the lens capsule.

Figure 20:
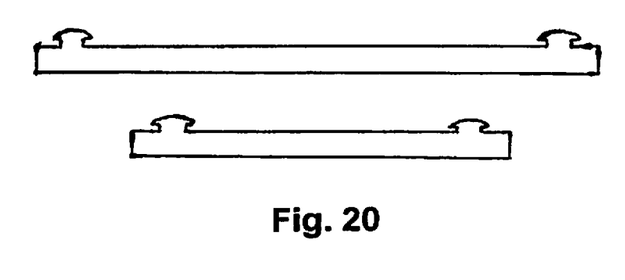
FIG. 20 shows two examples of a plug-type implant.

In another example embodiment of the invention, the implant is not a lens, but a plug, blank or bung. Such an implant is not required to have any refractive power, but serves merely to close a fenestration or other aperture in the capsule. An example of this is shown in FIG. 20. Indeed, FIG. 20 shows two examples of different diameter, depending on the size of the fenestration to be closed. It can be seen that this implant is flat and therefore has no optical power. Furthermore, the lugs in this situation are not required to accurately establish the rotational position of the implant (which would be the case with an asymmetrical lens), but merely to secure the plug to the capsule.

The plug may or may not be opaque, depending on the location of the aperture being closed.

A specific example of a plug in use with a capsule is not shown in the drawings. However, a typical scenario is as shown in FIG. 12, in which the lens was replaced by a plug such as shown in FIG. 20. The lugs engage with holes in one wall of the bag and block off an opening or fenestration, which might be larger than or smaller than the capsulotomy shown as item 86 in FIG. 12.

Fenestrations that might be closed off using the plug are, for example, fenestrations introduced into the capsule in order to facilitate the entry of an instrument for evacuating the lens material. In this respect, femtosecond lasers are often used to cut the lens into very small cubes or slices, so that they can be evacuated through a small-bore instrument or cannula. The cannula can be introduced into the capsule through such a fenestration. In addition, the plug can be used to provide tectonic support, in order to keep compartments in the eye physically separate. It is also useful as a means of preventing silicone oil from moving forward into the anterior segment of the eye. The plug may also be used to close or block a capsulotomy to inhibit vitreous prolapse.

Although a total of two lugs are shown in some embodiments and four in others, there may be as many lugs as there are haptics in the embodiment having haptics (there may also be fewer lugs than haptics), and fewer than, or more than, four lugs in the second. A criterion for selecting the number of lugs is to ensure a secure fixing of the implant to the capsule.

Also, it should be appreciated that the haptics shown in the example embodiment are representative only, and may take many other shapes.

The lugs, though shown as being unitary with the haptics or the lens extension, may instead be separate items, which are attached by suitable means to the haptics or extension in order to allow the lens optic to move or flex for accommodating lens designs. For flexible extensions a common material is silicone. The lugs may be constructed from silicone or acrylic material, as is common with current intraocular lens implants as well as other materials.

Similarly, while the implant, apart from the haptics, has been shown in the drawings as being essentially circular in shape, it may take any shape corresponding to the capsule opening against which it is to be located. Thus, where the implant is a lens, it may be oval or elliptical in shape, for example, instead of circular.

Although the use of the implant of the present invention has been described in connection with cataract surgery, alternative uses are envisaged. Thus, the implant can be also be employed in surgical procedures for treating myopia, hyperopia, astigmatism or presbyopia (refractive lens exchange surgery) or used in procedures where the natural lens is left in place and an implant lens is also inserted.

The foregoing description has been given by way of example only and it will be appreciated by a person skilled in the art that modifications can be made without departing from the scope of the present invention.

The invention claimed is:
1. An intraocular lens implant for placement in an eye to replace a natural lens of the eye, the implant comprising:

a main portion, which is a lamina presenting an X-Y plane extending therethrough, and a peripheral portion peripheral to the main portion, wherein an outermost perimeter of the lens implant lies on the X-Y plane, the implant having at least two lugs extending from the peripheral portion in a direction substantially perpendicular to the X-Y plane of the lamina, the at least two lugs being at least one of unitary with or attached to the peripheral portion and the at least two lugs being located at a radially outer edge of the lamina, the lugs being structured for fixed engagement with corresponding voids provided in a lens capsule of the eye, the lugs being structured to be secured in the voids to secure the implant in a fixed position in the capsule and wherein the lugs have a narrowed neck portion proximal to the peripheral portion-and an expanded head portion distal to the neck and the peripheral portion, the neck portion having a first diameter, the head portion having a second diameter, the first diameter being smaller than the second diameter and the neck having a length extending between the peripheral portion and the head, the length being equal to or greater than a thickness of the lens capsule, wherein the length of the neck portion is in a range of 30 to 50 micrometers, and wherein the neck portion has a diameter in a range of 100 to 500 micrometers.

2. The intraocular implant as claimed in claim 1, wherein the peripheral portion comprises at least two haptics extending from the main portion, the haptics comprising one of the at least two lugs extending from the haptics in said direction substantially perpendicular to the plane of the lamina.

3. The intraocular implant as claimed in claim 1, wherein the peripheral portion comprises a short extension of the main portion over the entire periphery of the main portion, the extension of the main portion comprising the at least two lugs.

4. The intraocular implant as claimed in claim 3, wherein the at least two lugs are substantially equidistantly spaced around the peripheral portion.

5. The intraocular implant as claimed in claim 1, wherein the lugs have a rounded top.

6. The intraocular implant as claimed in claim 1, wherein the head portion is mushroom-shaped.

7. The intraocular implant as claimed in claim 1, wherein the implant is a lens having refractive power, the main portion of the implant comprising an optic of the lens.

8. The intraocular implant as claimed in claim 1, wherein the neck portion of the lugs has straight parallel sides when viewed in cross section.

* * * * *